(12) United States Patent
Wieser

(10) Patent No.: US 10,186,025 B2
(45) Date of Patent: Jan. 22, 2019

(54) INSPECTION SYSTEM AND METHOD FOR DEFECT ANALYSIS OF WIRE CONNECTIONS

(71) Applicant: WiTrins s.r.o, Hovorcovice (CZ)

(72) Inventor: Roman Franz Wieser, Hovorcovice (CZ)

(73) Assignee: WITRINS S.R.O, Hovorcovice (CZ)

( * ) Notice: Subject to any disclaimer, the term of this patent is extended or adjusted under 35 U.S.C. 154(b) by 49 days.

(21) Appl. No.: 15/180,837

(22) Filed: Jun. 13, 2016

(65) Prior Publication Data

US 2016/0364854 A1 Dec. 15, 2016

(30) Foreign Application Priority Data

Jun. 12, 2015 (DE) .......................... 10 2015 109 431

(51) Int. Cl.
*G06T 7/00* (2017.01)
*G01B 11/06* (2006.01)
(Continued)

(52) U.S. Cl.
CPC ........ *G06T 7/0004* (2013.01); *G01B 11/0608* (2013.01); *G01B 11/24* (2013.01);
(Continued)

(58) Field of Classification Search
CPC ......... G06T 7/0004; G06T 2207/30148; G06T 2207/10048; G06T 2207/10024;
(Continued)

(56) References Cited

U.S. PATENT DOCUMENTS 5,247,344 A 9/1993 Doan
7,039,228 B1 * 5/2006 Pattikonda ......... G01B 11/0608
348/87

(Continued)

FOREIGN PATENT DOCUMENTS

DE 4218971 A1 12/1993
DE 19609045 7/1997
(Continued)

OTHER PUBLICATIONS

"Understanding Line Scan Camera Applications." Teledyne, Aug. 1, 2014. http://leadwise.mediadroit.com/files/292072069_TD. LineScanApp_whitepaper.v4.pdf. Accessed Dec. 18, 2017.*

(Continued)

*Primary Examiner* — Geoffrey E Summers
(74) *Attorney, Agent, or Firm* — Billion & Armitage; Michael A. Collins

(57) ABSTRACT

The invention relates to an inspection system (10) for defect analysis of a wire connection (11) between a substrate (13) and a semiconductor component (15, 16) of a product (12), the inspection system comprising a first projection device (24), a line scan camera (28) and a processing device, the first projection device having at least one slit projection means (25), the slit projection means being capable of projecting a light slit (33) onto a wire (21, 22) of the wire connection, light of the light slit reflected by the wire in a detection plane (39) of the line scan camera extending perpendicularly, preferably orthogonally to a substrate surface (14) being detectable by means of the line scan camera, analysis image information of the product being derivable from a plurality of line scan image information of the line scan camera by means of the processing device, wherein the slit projection means is arranged in relation to the line scan camera in such a manner that the light slit can be projected onto the product so as to extend within the detection plane, the inspection system comprising a second projection (Continued)

device, the second projection device having at least one illuminating means (27), the illuminating means being capable of projecting diffuse light onto the product, light of the diffuse light reflected by the product in the detection plane being detectable by means of the line scan camera.

19 Claims, 6 Drawing Sheets

(51) Int. Cl.
  G01B 11/24    (2006.01)
  H04N 5/225    (2006.01)
  H04N 5/33     (2006.01)
  H04N 5/369    (2011.01)
  G01N 21/956   (2006.01)

(52) U.S. Cl.
  CPC ......... *G01N 21/956* (2013.01); *H04N 5/2256* (2013.01); *H04N 5/332* (2013.01); *H04N 5/3692* (2013.01); *G01N 2021/95661* (2013.01); *G06T 2207/10024* (2013.01); *G06T 2207/10048* (2013.01); *G06T 2207/30148* (2013.01); *H01L 2224/48227* (2013.01); *H01L 2224/48472* (2013.01); *H01L 2224/49175* (2013.01); *H01L 2224/859* (2013.01)

(58) Field of Classification Search
  CPC ..... G06T 7/0006; G06T 7/0008; G06T 7/001; G06T 2207/30108; G06T 2207/30141; G06T 2207/30152; G06T 7/521; G06T 7/586; G01N 21/956; G01N 2021/95661; H04N 5/2256; H04N 5/3692; H04N 5/332; G01B 11/0608; G01B 11/24; H01L 2224/859; H01L 2224/48472; H01L 2224/48227; H01L 2224/49175
  USPC ................ 382/141, 145, 146, 147, 149, 150
  See application file for complete search history.

(56) References Cited

U.S. PATENT DOCUMENTS 8,244,023 B2 * 8/2012 Yamada ................... G06T 7/521
                                                   359/559
2003/0059103 A1    3/2003 Shiomi et al.
2004/0239950 A1 * 12/2004 Mahon ................... G01B 11/24
                                                   356/606
2005/0157920 A1 *  7/2005 Doherty ............. G01B 11/2513
                                                   382/145
2010/0177951 A1 *  7/2010 Vodanovic ......... G01B 11/0608
                                                   382/141
2010/0195114 A1    8/2010 Mitsumoto et al.
2012/0033066 A1    2/2012 Wieser
2012/0105859 A1    5/2012 Heo et al.
2012/0133741 A1    5/2012 Wagner

FOREIGN PATENT DOCUMENTS

| DE | 10100892 A1 * | 7/2002 | ....... G01N 21/95684 |
| DE | 10100892 A1 | 7/2002 | |
| DE | 10208978 A1 | 9/2003 | |
| DE | 10319543 | 11/2004 | |
| DE | 102005031490 A1 | 2/2007 | |
| DE | 102012104282 | 11/2013 | |
| DE | 102012104745 | 12/2013 | |
| EP | 0935135 A1 * | 8/1999 | ....... G01N 21/95684 |
| EP | 2307852 B1 | 5/2012 | |
| JP | 07037955 A * | 2/1995 | ............ H01L 24/48 |

OTHER PUBLICATIONS

"Output Couplers." RP Photonics, Jul. 8, 2008. https://www.rp-photonics.com/output_couplers.html.*
"Introduction to Laser Spatial Filtering." AZO Optics, Apr. 23, 2014. https://www.azooptics.com/Article.aspx?ArticleID=901.*
"Solder Bump Bonding, Ball Bumps and Wire Bonds." PTI Blog. May 24, 2010.*
Perng, Der-Baau, Cheng-Chuan Chou, and Shu-Ming Lee. "Illumination system for wire bonding inspection." Applied optics 46.6 (2007): 845-854.*
Zhang, W., L. M. Koh, and Eddie MC Wong. "Computer vision system for the measurement of IC wire-bond height." TENCON'93. Proceedings. Computer, Communication, Control and Power Engineering. 1993 IEEE Region 10 Conference on. vol. 2. IEEE, 1993.*
"IPSO Search Report", dated Apr. 25, 2018.

* cited by examiner

INSPECTION SYSTEM AND METHOD FOR DEFECT ANALYSIS OF WIRE CONNECTIONS

CROSS REFERENCE TO RELATED APPLICATION

This application claims benefit of application Ser. No. 102015109431.2, filed on Jun. 12, 2015 in Germany and which application is incorporated herein by reference. A claim of priority is made.

SUMMARY

The invention relates to an inspection system and to a method for defect analysis of a wire connection between a substrate and a semiconductor component of a product, the inspection system comprising a first projection device, a line scan camera and a processing device, the first projection device having at least one slit projection means, the slit projection means being capable of projecting a light slit onto a wire of the wire connection, light of the light slit reflected by the wire in a detection plane of the line scan camera extending perpendicularly, preferably orthogonally to a substrate surface being detectable by means of the line scan camera, analysis image information of the product being derivable from a plurality of line scan image information of the line scan camera by means of the processing device.

With the inspection system described above and with the method for defect analysis of a wire connection, wire connections and bonds produced by what is known as wire bonding are analyzed for possible defects. The semiconductor component can be an integrated circuit, such as a chip, or a discrete semiconductor component, such as a transistor or a light-emitting diode, the semiconductor component being connected to terminal faces of a substrate via a wire or bond wire. The terminal face of the substrate can be connected to a terminal face of the semiconductor component by means of methods sufficiently known from the state of the art, such as TC, TS or US bonding. The wire used is usually made of gold, aluminum, silver or copper and can have a diameter of 10 to 500 μm. So-called thin wires have a diameter of 10 to 20 μm and allow narrow structures of the terminal faces and thereby particularly high packing densities. When wire connections of this kind are produced by wire bonding, however, defects may occur, such as touching adjacent wires or a wire end not in contact with a terminal face. Hence, the corresponding products and wire connections are optically analyzed for defects.

Methods are known from the state of the art in which images of wire connections between a substrate and a semiconductor component are taken by means of a video camera and processed. The product to be analyzed is illuminated and image information captured by the video camera is processed in order to recognize the respective wire connections and is analyzed for defects. For example, it is known for wire connections to be individually approached by a matrix camera, which is relatively time-consuming and thus cost-intensive in case of a plurality of wire connections and semiconductor components on a substrate. Furthermore, it is known for the substrate having a semiconductor component and the respective wire connections to be completely scanned in one pass by means of a line scan camera. In this case, the area of detection of the line scan camera on the product is illuminated with obliquely incident light from two directions, each parallel to the length of the line scan camera. In this way, shadows from the wires of the wire connections or semiconductor components as those occurring in case of the use of a single incident light are supposed to be prevented. The use of incident light only is unsuitable in case of overlapping wire connections because of shadowing.

To achieve a particularly reliable measuring result, however, it is still necessary in the known methods for defect analysis to perform multiple passes or scans of the product at the inspection system, possibly also in order to detect different types of defects. The problem with image processing of the collected image information is reliably recognizing the respective wire connections and potentially associating the image information with one another in case of multiple passes. This is comparatively time-consuming and thus accompanied by high costs because of the consequently required passes of the product at the inspection system and of the amount of data collected.

Therefore, the object of the present invention is to provide an inspection system and a method for defect analysis of wire connections that allows reliable and quick defect analysis.

This object is attained by an inspection system having the features of claim 1 and by a method having the features of claim 14.

The inspection system according to the invention for defect analysis of a wire connection between a substrate and a semiconductor component of a product comprises a first projection device, a line scan camera and a processing device, the first projection device having at least one slit projection means, the slit projection means being capable of projecting a light slit onto a wire of the wire connection, light of the light slit reflected by the wire in a detection plane of the line scan camera extending perpendicularly, preferably orthogonally to a substrate surface being detectable by means of the line scan camera, analysis image information of the product being derivable from a plurality of line scan image information of the line scan camera by means of the processing device, wherein the slit projection means is arranged in relation to the line scan camera in such a manner that the light slit can be projected onto the product so as to extend within the detection plane, the inspection system comprising a second projection device, the second projection device having at least one illuminating means, the illuminating means being capable of projecting diffuse light onto the product, light of the diffuse light reflected by the product in the detection plane being detectable by means of the line scan camera.

In particular because the light slit can be projected onto the wire so as to extend within the detection plane, the wire located in the detection plane can be illuminated substantially solely in the detection plane from obliquely above, i.e. with the light slit as incident light. The line scan camera, too, is thus focused on the wire, which means that the wire can be detected very well. In this way, it becomes possible to significantly improve detection of a wire in subsequent image processing of the analysis image information and to avoid errors. The plurality of one-dimensional line scan image information of the line scan camera is combined or put together in the processing device to form the two-dimensional analysis image information. Thus, with the inspection system, the product can be scanned via the line scan camera by moving the product in relation to the inspection system. The light slit preferably extends vertically in relation to the substrate or semiconductor component and is directed or collimated at least in the longitudinal direction of a cross-section of the light slit. By way of the thus improved detection of a wire connection, it becomes possible for a product to undergo reliable defect analysis in as little as one pass or scan.

Furthermore, diffuse and homogenous light can be projected onto the product by means of the illuminating means, the line scan camera being capable of capturing reflected light of the diffuse light in the detection plane. In this way, it becomes possible to determine a location of the semiconductor component on the substrate and a relative position of the wire connections or wires by image processing by means of the processing device. Furthermore, potential shadows can also be illuminated with the diffuse light by means of the directed light of the light slit and thus be captured or detected. The product can be illuminated with the diffuse light by the illuminating means or second projection device in a separate pass of the product with the inspection system or also together with projection of the light slit in one pass only.

Optionally, instead of an original line scan camera, a contact imaging sensor (CIS) or an area scan camera can be employed, in which only one or few lines are used as in the case of a line scan camera.

The line scan camera can be arranged perpendicularly to a direction of movement of a product, the detection plane then extending parallel or perpendicularly to the wire. In this way, it becomes possible for the wires to be detected substantially completely or at least partially in a single capture of the line scan camera or in line scan image information of the line scan camera. Consequently, in this case, the wires to be examined are arranged perpendicularly to the direction of movement of the product when the product passes through the inspection system. In this case, it may be provided for the product to be aligned with the length of the wires or wire connections in relation to the line scan camera, for example. If the product does not have parallel wire connections only, but also wire connections that are offset by 90 degrees, for example, two passes in the inspection system at a correspondingly adjusted alignment of the product in relation to the line scan camera may be provided, as well.

The slit projection means can be arranged parallel in relation to the line scan camera and can have a partially transparent mirror arranged within the detection plane between the product and the line scan camera, and the light slit can be deflected into the detection plane via the partially transparent mirror. Consequently, the light slit is coupled into the detection plane via the partially transparent mirror or semitransparent mirror, and the line scan camera thus looks onto the product or substrate surface in the same plane. In this way, a surface of the substrate can be illuminated, whereas the wire or bond wires tend to appear dark because a reflecting surface of the wire immediately reflects the light of the light slit into another direction. Areas of the wire that are parallel to the line scan camera and to the slit illumination are the only areas that can reflect parts of the light slit directly into the line scan camera. However, since the wires usually bridge a distance between terminal faces as arcs, a direct reflection is possible for only extremely small parts of the slit illumination. This means that a negative image of the wire can be generated and obtained in addition to the image information obtained by means of the illuminating means.

Alternatively or additionally, the slit projection means can be arranged laterally perpendicularly in relation to the line scan camera as another slit projection means, and the light slit can be projected onto the wire in such a manner that the semiconductor component is unlit by the light slit. In this case, the slit projection means can be arranged at a longitudinal end of the line scan camera. In this way, it is also ensured that the light slit extends within the detection plane. The light slit can also be projected onto the wire laterally from above. Consequently, the light slit extends flush with the line scan camera in relation to the line scan camera and perpendicularly or orthogonally to the direction of movement. The fact that the light slit extends solely within the detection plane and can consequently be projected onto the product laterally beside the camera provides the option of not illuminating the semiconductor component and, if applicable, not the substrate, either, with the light slit and to leave them unlit. Since this means that at lest the semiconductor component is not illuminated by the light slit, the semiconductor component will substantially not appear at all or visibly dark at high contrast in relation to the wire directly illuminated by the light slit in the analysis image information and in the captured image of the product.

Advantageously, the slit projection means can have at least one screening shade for blocking the light slit from the semiconductor component and, if applicable, from the substrate, the light slit being projectable onto the wire at an acute angle α in relation to a surface of the product. The screening shade thus allows delimiting the light slit so that the light slit hits only the wire or, if applicable, the substrate. It may be provided that both a height of the slit projection means in relation to the surface of the product and the screening shade are adjustable. Furthermore, the slit projection means can have another screening shade for blocking the light slit from the line scan camera so that the light of the light slit is prevented from falling into the line scan camera. If the slit projection means and the screening shade are variably adjustable, the inspection system and the slit projection means can be adjusted to different products, making the inspection system flexibly employable for these products. When adjusting the slit projection means, the screening shade or the slit projection means itself can be arranged in such a manner that the light slit is incident on the wire and on the substrate at angle α without visibly illuminating the semiconductor component, for example.

The slit projection means can have an assembly of optical elements, an aperture diaphragm and/or a light guide assembly, and the light slit can be a collimated light slit. The optical elements can be one or more lenses or cylinder lenses, for example. The aperture diaphragm can be slit-shaped to match the shape of the light slit while other aperture diaphragms and a combination of the aperture diaphragm with optical elements may be envisaged, as well. Moreover, a light guide assembly may be provided, which can be composed of a single light guide in the shape of a slit or of a plurality of optical fibers, which are arranged in the shape of a slit. Light-emitting diodes can serve as a light source, for example. For instance, a light-emitting diode for coupling light into the light guide assembly or a plurality of light-emitting diodes in a series arrangement can be provided. The use of a light guide assembly is particularly advantageous in that the light sources will be arranged at larger distances and the slit projection means can consequently be formed comparatively small in an area beside the line scan camera and/or parallel thereto and thus in an easily adjustable or positionable manner. The illuminating means can have an arc-shaped diffuser, which can be arranged laterally parallel in relation to the line scan camera and orthogonally to a direction of movement of a product. If the diffuser is arc-shaped, the diffuser can be adjusted particularly well to a shape of the wire, allowing improved illumination of the wire for capture by the line scan camera. Furthermore, this also ensures that potential shadowing by the wire or by component edges of the semiconductor component is avoided because the wire and the semiconductor component can be illuminated from multiple sides by the arc-shaped diffuser. This is also especially advantageous in particular if there are multiple overlapping wire connections, such as on a chip having terminal faces offset by height. The arc shape of the diffuser further allows for the diffuser to approach the product area to be analyzed or the semiconductor component very closely. If the product or the semiconductor component is already installed in a housing or if the semiconductor component is already installed in a chip package, the diffuse light can be brought into immediate proximity to the wire connections by moving the arc-shaped diffuser at least partially into the housing or arranging it therein. In this way, potential shadowing by the housing can be avoided, as well. The diffuser can also be provided with a diaphragm or aperture, which is realized in such a manner that the substrate or the semiconductor component is substantially unlit. Moreover, the arc-shaped diffuser or the illuminating means can be realized so as to be adjustable in such a manner that the arc-shaped diffuser is moved on the inspection system and is adjusted to a geometry of the product to be examined in each case. Additionally, the illuminating means can have a plane diffuser, and the plane diffuser can be arranged parallel in relation to the product. In this way, the product or substrate can be additionally illuminated with diffuse light directly from above, i.e. orthogonally in relation to the product or substrate. Thereby, other independent information can be obtained.

The illuminating means can have a light guide assembly or light-emitting diodes in an arc-shaped and/or plane arrangement. The light guide assembly can be a single light guide or a bundle of optical fibers into each of which light is coupled by light-emitting diodes, for example. The substantial aspect is that when optical fibers are used, the light source can also be arranged remotely from the actual illuminating means, which makes the illuminating means compact and easily adjustable. Depending on the design of the light guide assembly or of the light-emitting diodes, they can be used plane and/or arc-shaped only together with a plane or arc-shaped diffuser, respectively, such as a diffuser plate or film.

The illuminating means and/or the slit projection means can emit light in the wavelength ranges red, green and blue (RGB), infrared (IR) and/or ultraviolet (UV). Thus, it becomes possible in particular to use polychromatic light, so-called white light in the visible range, for illumination. It may also be provided that color portions of the light are selected at will to mix certain wavelength ranges. For example, blue and yellow light is suitable for illuminating the material gold, whereby wires consisting of gold will be especially easily detectable by means of the line scan camera. Depending on the material used for the substrate, for the semiconductor component and for the respective terminal faces, a high color contrast can be achieved. Also, the illuminating means and the slit projection means can thus be operated synchronously with a movement of the product relative to the inspection system and in a single pass of the product or also separately from one another and in a serially clocked manner. It may further be envisaged that the illuminating means and/or the slit projection means has/have a polarization filter.

In an advantageous embodiment of the inspection system, basic colors can be detected by means of the line scan camera, and information regarding a surface of a product can be derivable from a color value of the line scan image information by means of the processing device. Thus, the line scan camera can not only detect gray values, but also have at least two or three parallel rows of pixels for detecting the basic colors red green and blue. In particular if the product is illuminated with different basic colors, the basic colors can be separated especially well; i.e., simultaneous illumination with different colors can take place. Moreover, at least information regarding the surface of the product can be derived via the color value of the line scan image information. Said information may be material information or information regarding surface properties, for example.

Preferably, the first projection device can have a second slit projection means, and the second projection device can have a second illuminating means, and the first and second slit projection means and the first and second illuminating means can be arranged coaxially in relation to the line scan camera. In particular semiconductors contacted at their periphery, such as chips or bare dies, can thus be analyzed especially quickly because two parallel longitudinal sides of the semiconductor each having wire connections can be illuminated simultaneously. Additionally, the coaxial arrangement in relation to the line scan camera leads to a uniform illumination of the wire connections and of the product.

The inspection system can also have another line scan camera, which can be arranged parallel to the line scan camera or first line scan camera. The other line scan camera, which is arranged parallel, thus allows detecting line scan image information and to derive analysis image information of the product simultaneously with the first line scan camera. Consequently, the other line scan camera has another detecting plane, the other detecting plane intersecting the detecting plane or first detecting plane in the area of the product or wire to be analyzed, which means that the other detecting plane can no longer be arranged orthogonally to the surface of the product or to the substrate surface. For example, height information of the wire or semiconductor component in relation to a surface of the product or a substrate surface can thus also be determined by triangulation by means of the other line scan camera. Moreover, it becomes possible to also safely detect overlapping wires. Any potentially present shadowing has little significance for the result of the analysis because of the parallel capture by the other line scan camera.

In the method according to the invention for defect analysis of a wire connection between a substrate and a semiconductor component of a product using an inspection system, the inspection system comprises a first projection device, a line scan camera and a processing device, the first projection device having at least one slit projection means, the slit projection means being capable of projecting a light slit onto a wire of the wire connection, light of the light slit reflected by the wire in a detection plane of the line scan camera extending perpendicularly, preferably orthogonally to a substrate surface being detected by means of the line scan camera, analysis image information of the product being derived from a plurality of line scan image information of the line scan camera by means of the processing device, wherein the light slit is projected onto the product so as to extend within the detection plane, the inspection system comprising a second projection device, the second projection device having at least one illuminating means, diffuse light being projected onto the product by means of the illuminating means, light of the diffuse light reflected by the product in the detection plane being detected by means of the line scan camera.

With respect to the advantageous effects of the method according to the invention, reference is made to the description of advantages of the inspection system according to the invention.

By means of the processing device, an offset can be superimposed on the plurality of line scan image information of the line scan camera in a direction of movement of the product, and the offset can be smaller than a physical image resolution of the line scan camera. When scanning the product by means of the inspection system, the product can be illuminated in a first position by the slit projection means and/or by the illuminating means and can then be moved into a second position and subsequent positions relative to the line scan camera, line scan image information being detected analogously to the first position. In this way, a scan of an entire surface of the product or of only the wire connections of the product can be carried out, the product or the wire connections thus having been completely illuminated by the projection devices. It may be provided that an offset between the first position and the second position and subsequent positions follows at an overlap of at least ⅓ pixels. If a wire has a diameter of 18 μm, for example, the product can be moved from the first position into the respective subsequent position in steps of 2 μm, which means that a resolution of the corresponding image or of the analysis image information of 3 to 8 μm can be achieved. In this way, full-resolution or analysis image information can be obtained, potentially undetected image areas being below a possible resolution of the line scan camera. Furthermore, it is also possible to detect any number of n color images in one scan, the n color images representing n information possibilities. In this context, as a function of the product features to be inspected, variations can be correspondingly adopted in terms of illumination level, light color, illumination angle and illumination technology. The product can be moved once in the direction of an X-axis and/or a Y-axis of the product in relation to the line scan camera and can be optically scanned, and analysis image information associated with the projection devices can be obtained. Depending on the arrangement of the wire connections, the product can be moved in the direction of the X-axis and, if required, subsequently be moved once in the direction of the Y-axis in relation to the line scan camera. This can be made possible in particular in that the projection devices and the line scan camera can be synchronized, the synchronization allowing the analysis image information to be associated. In this way, a defect analysis of a product can be limited to a one-time scan of the surface of the product or of the wire connections and thus be significantly shortened and simplified.

Furthermore, the product can be optically scanned in at least two planes of a Z-axis of the product. Since the wire connections or wires are usually arranged in an arc shape standing upright on the surface of the product, it may be required to vary a focus of the line scan camera in order to fully capture a wire or to change a distance between the line scan camera and the product in order to achieve an entirely sharp image of the wire. Depending on the height of the wire in relation to the surface or extension in the Z-axis, the product or the area in question of the wire connections can be scanned in at least two planes of the Z-axis.

To be able to conduct a defect analysis of the product or of the wire connections as quickly as possible, the light beams or the light of the projection devices can be projected onto the product in a time sequence, and the line scan camera can be synchronized with the projection devices. For example, a product can be moved below the line scan camera in the direction of an X-axis, an examination area of the surface of the product being illuminated by means of the first projection device or slit projection means at first in order to detect a geometrical location of a wire in a first position, the line scan camera capturing image information of the surface area. The image information can be processed and stored by the processing device by means of a frame grabber. Subsequently, the surface area can be illuminated by the second projection device or by the illuminating means and corresponding image information, such as material information, can be registered by the line scan camera and be processed by the processing device. In case of the second projection device, it may also be provided that the surface area is successively illuminated with light in the basic colors red, green and blue, the line scan camera being capable of registering the basic colors separately from each other. This means that a series of different image information can be serially registered for the surface area of the first position. For this purpose, it will be necessary that the line scan camera is synchronized with the projection devices. For example, if red light is projected onto the product by means of the second projection device, it may be provided that red light is registered by the line scan camera for the duration of projection. Alternatively, it is also possible that the line scan camera registers the basic colors separately from each other or together, but that an association of the image information with the respective illuminating situation is always possible. In particular if the basic colors are registered successively or serially for one position, a full-resolution image or analysis information of the product can be obtained.

Height information and/or geometrical information of the wire can be obtained from a distribution of the light beam reflected by a surface of the wire by means of the processing device. The processing device can be configured in such a manner that the processing device can obtain a relative position of the light slit on the surface of the product or wire from a distribution of the light slit of the slit projection means reflected by the surface of the product or wire. The processing device can obtain geometrical information of the wire, for example, from a reflection image of the product or wire based on a normal distribution of a light density. In this way, a maximum value or maximum of the density function of the normal distribution of the light density on the surface of the wire can be determined, as well, from which height information can also be derived. Alternatively, it is also possible to obtain height information of the wire by triangulation with the aid of a second line scan camera arranged parallel to the line scan camera or first line scan camera.

It may in particular be provided that the light of the homogenous or diffuse light reflected by the product is analyzed by means of the processing device in terms of hue, brightness and/or saturation. In this way, the processing device can analyze the analysis image information or RGB color image information separately in terms of hue, saturation and value in a color space (HSV, HSL, HSB). The image information can also be used in particular for analyzing the material type and distribution because different materials have different H, S and V-values. A color space can be selected as a function of the materials to be analyzed, and an RGB color space may serve as a basis.

Thus, a material and/or a material property of a product can be determined by means of the processing device from the analysis image information obtained by the second projection device.

Other information regarding material and structure of a product can be obtained if analysis image information associated with the projection devices are superimposed and evaluated by means of the processing device. With a combination of analysis image information, such as in case of high-dynamic-range images (HDRI), a higher contrast improvement can be achieved, for example, and material mixtures on a surface of the product can be analyzed, as well. Especially surfaces having a very weak contrast can thus be inspected in a combined manner. At least two analysis image recordings of an area of wire connections, for example, are recorded with different brightness or at different illumination levels and are combined by means of image processing of the processing device. Optionally, sequential illumination can be performed by means of the slit projection means and the illuminating means. In this case, a first line scan image information or analysis image information is recorded under illumination by the slit projection means only, and a second line scan image information or analysis image information is recorded under illumination by the illuminating means only. The respective analysis image information is subsequently combined by means of image processing. In this way, not only a position of the wire connections but also a position of terminal faces can be recognized.

Furthermore, in the course of defect analysis, analysis image information can be compared to reference image information by means of the processing device. The reference image information of the product or of the respective wire connections can comprise CAD data and material distribution data of the product. The comparison can take place by way of image processing, and difference images for different structures of the product and arrangements of wires, respectively, can be analyzed separately in each case. Furthermore, the material information can be combined with height information in order to clearly identify a wire, for example. Accordingly, the reference image information can comprise all geometrical data of the product, material information, component information and height information. If the analysis image information deviates from the reference image information, a defect can be signalized. However, this is not absolutely necessary if tolerance ranges are defined, which allow geometrical deviation of a wire connection from a reference position, for example. In this way, adjacent wire connections can approach each other or be apart from each other within the tolerance range as long as a short-circuit is avoided. This examination of a difference image thus requires a clear association of the analysis image information with the reference image information. In principle, however, a comparison of the analysis image information with the reference image information is not necessarily required. For instance, it may suffice for a defect analysis to simply detect a location of respective the wire connections and to signalize a defect if the respective wire connections approach each other within a defined tolerance range.

Other advantageous embodiments of the method become apparent from the feature descriptions of the dependent claims back-referenced to the device claim.

DESCRIPTION OF FIGURES

Hereinafter, a preferred embodiment of the invention will be explained in more detail with reference to the accompanying drawing.

In the drawing.

DETAILED DESCRIPTION

Figure 1:
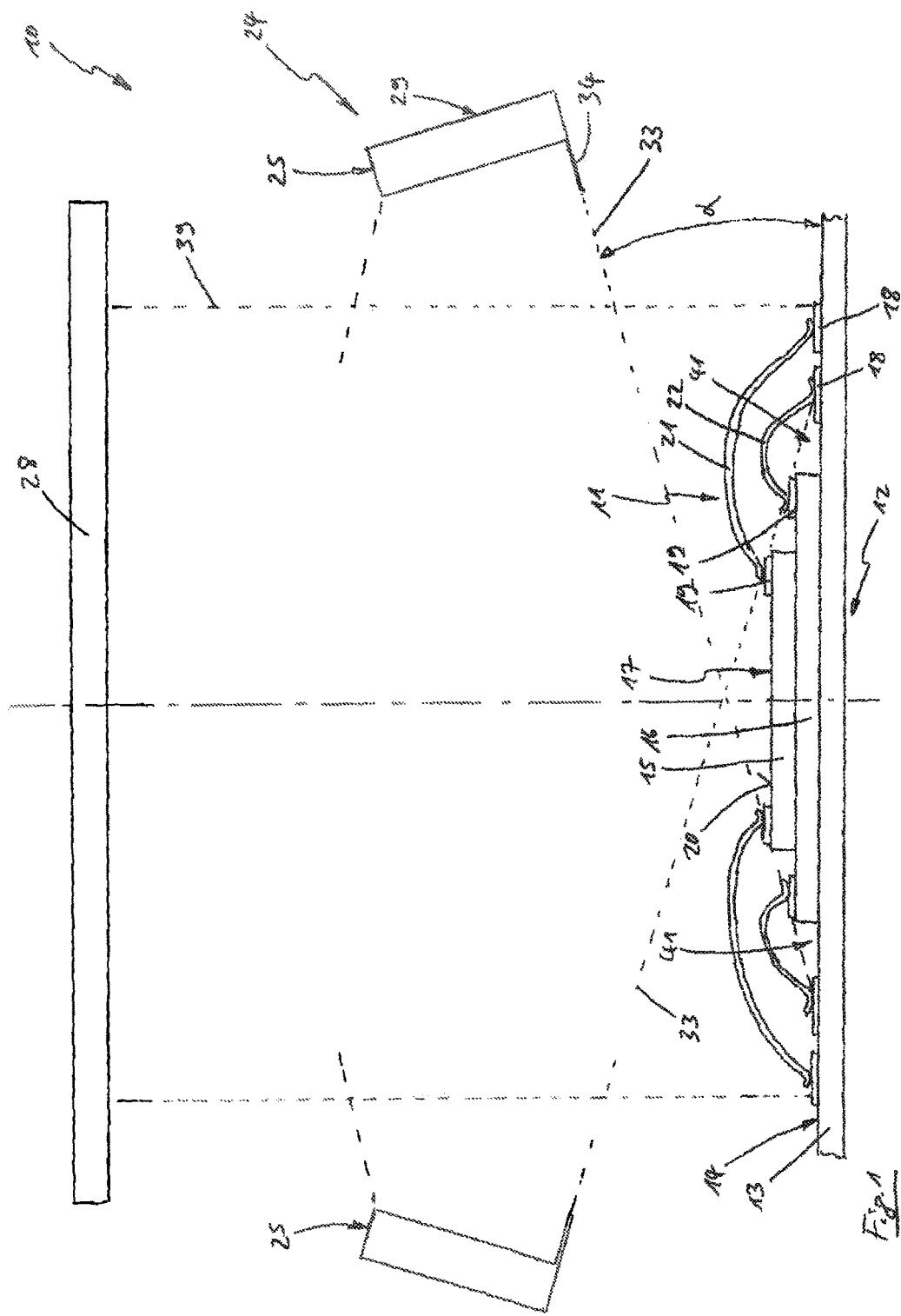
FIG. 1 shows a schematic diagram of an embodiment of an inspection system in a front view.

A combined view of FIGS. 1 to 7 shows an inspection system 10 for defect analysis of wire connections 11 of a product 12. The product 12 comprises a substrate 13 on whose surface 14 two semiconductor components 15 and 16 are arranged one on top of the other. The semiconductor components 15 and 16 form a chip 17. The wire connections 11 are formed between terminal faces 18 on the surface 14 of the substrate 13 and terminal faces 19 on a surface 20 of the chip 17 or of the semiconductor components 15 and 16 together with wires 21 and 22 connecting the terminal faces 18 and 19. The product 12 has already been inserted into a housing 23.

Figure 2:
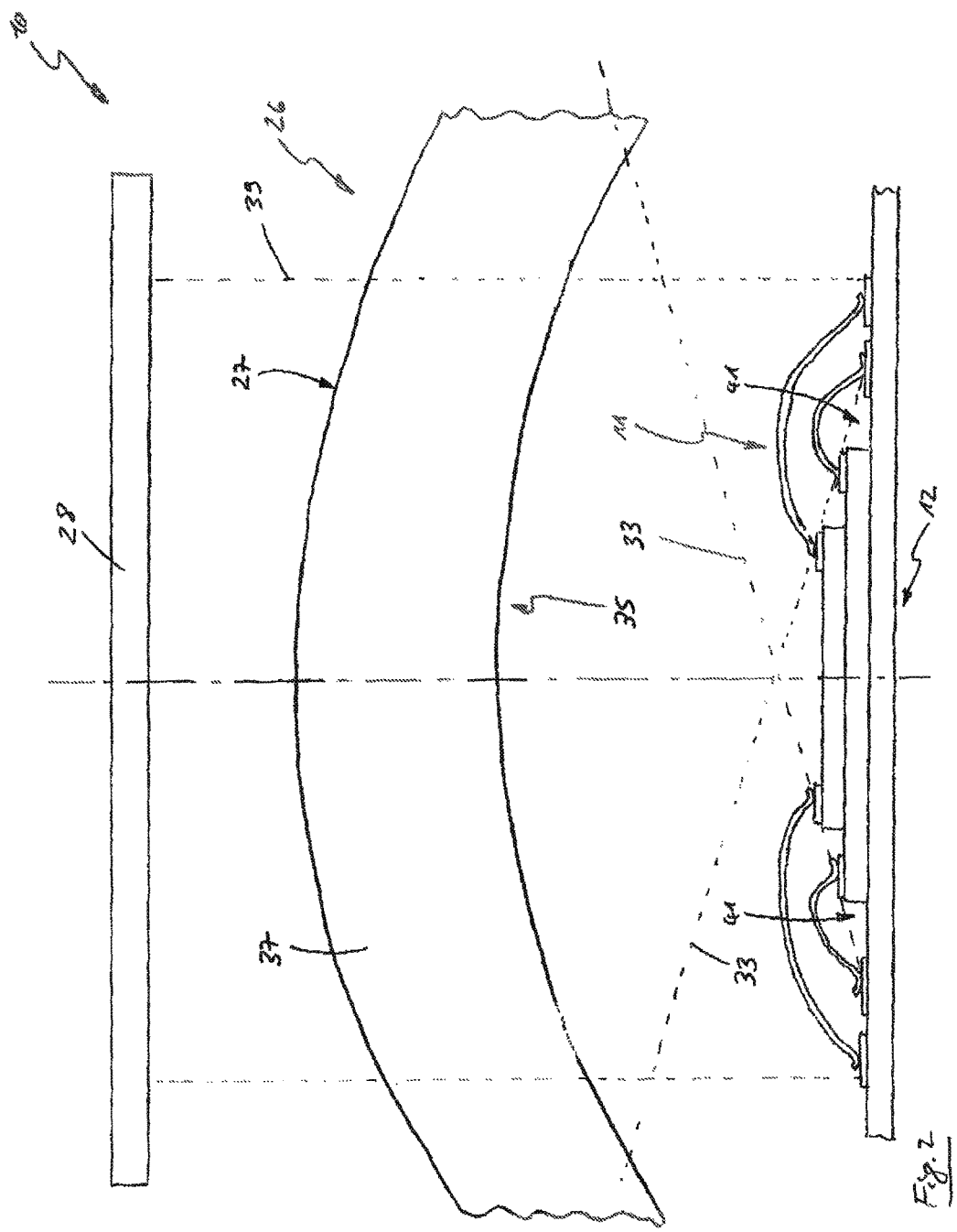
FIG. 2 shows a schematic diagram of the inspection system in a front view.
Figure 3:
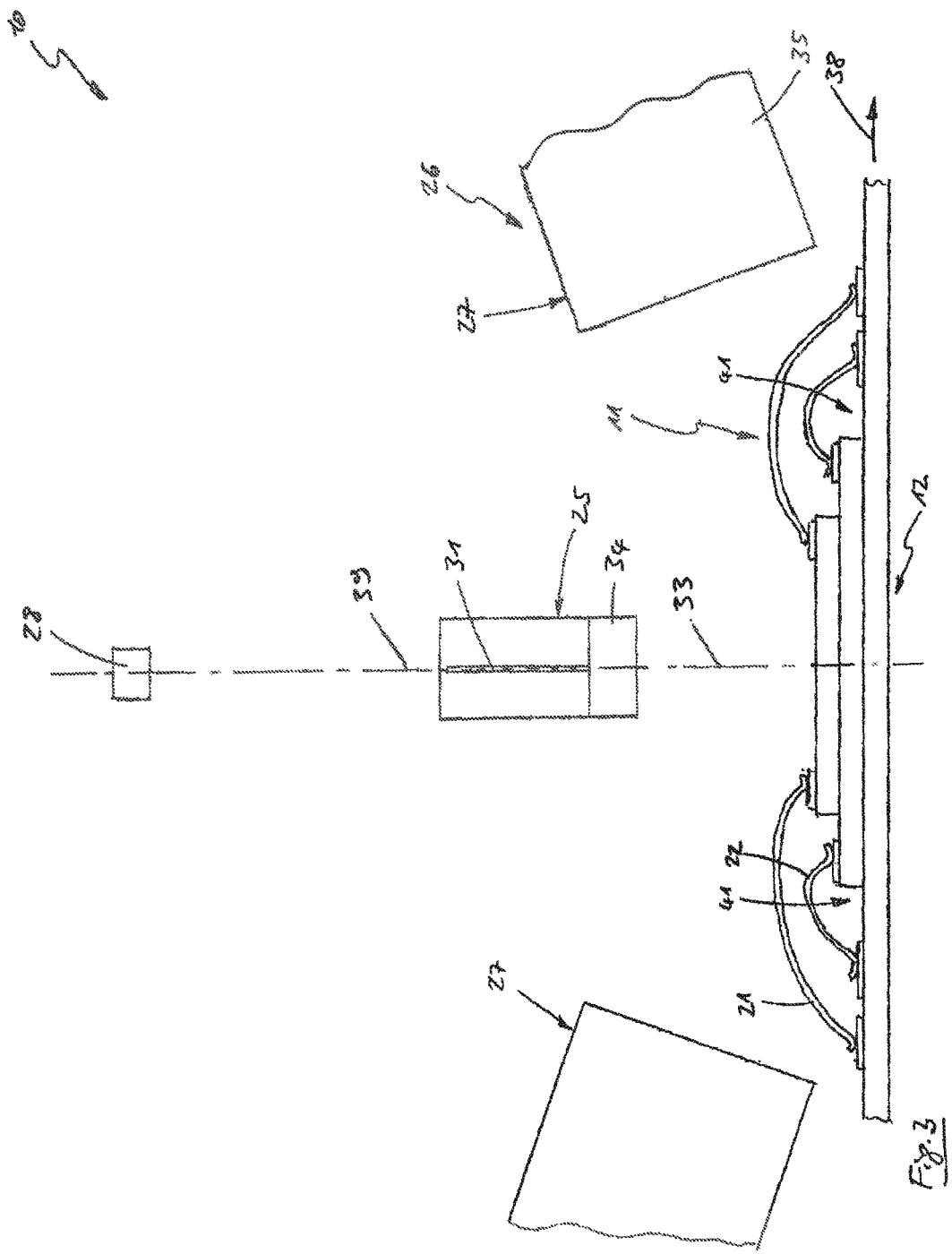
FIG. 3 shows a schematic diagram of the inspection system in a lateral view.

The inspection system 10 comprises a first projection device 24 having two slit projection means 25, a second projection device 26 having two illuminating means 27, and a line scan camera 28 as well as a processing device (not illustrated) for processing line scan image information obtained by means of the line scan image camera 28. The line scan camera 28 is configured in such a manner that basic colors can be registered by the line scan camera 28. FIGS. 1 and 2 show the first projection device 24 and the second projection device 26, respectively, separately from each other for simplified illustration.

The slit projection means 25 has a support 29 having a light guide assembly 30. The light guide assembly 30 is composed of optical fibers, which are led to the support 29 in bundles and are arranged in the shape of the slit 31 illustrated here. The support 29 further forms an aperture diaphragm 32 for forming a light slit 33. The light required therefor is coupled into the optical fibers (not illustrated). Moreover, a screening shade 34 is arranged on the support 29, which delimits the substantially collimated light slit 33.

The illuminating means 27 has a housing 35 and an arc-shaped diffuser 36. The diffuser 36 is formed by a plastic film 37. Light-emitting diodes (not illustrated) are arranged within the housing 35, and diffuse homogenous light in the basic colors (RGB) can be emitted onto the product 12 by the illuminating means 27 via the diffuser 36.

The line scan camera 28 is arranged above the product 12, the product 12 being movable relative to the line scan camera 28 in the direction of an arrow 38. It is basically immaterial whether it is the product 12 or the inspection system 10 that is moved. The line scan camera 28 forms a detection plane 39, which extends orthogonally to the surface 14 of the substrate 13 but, in principle, can also be arranged in deviation thereof perpendicularly to the surface 14. The product 12 is moved completely through the detection plane 39 along a path of movement 40 so that the product 12 can be optically scanned by the line scan camera 28. Each of the slit projection means 25 and the illuminating means 27 is arranged coaxially to the line scan camera 28. The light slit 33 generated by the slit projection means 25 extends solely within the detection plane 39 and is subsequently superimposed with the detection plane 39. The light slit 33 is arranged and formed by way of the arrangement of the slit projection means 25 and with the aid of the screening shade 34 in such a manner that the light slit 33 is blocked from the chip 17 and illuminates the wires 21 and 22 and, in part, the substrate 13. To this end, the light slit 33 is projected onto the wires 21 and 22 at an angle α in relation to the surface 14 of the substrate 13. This means that the chip 17 is not illuminated or only minimally illuminated by the light slit 33. Furthermore, an area 41 of the substrate 13 below the wires 21 and 22 is not illuminated by the light slit 33, either. The surface 20 and the area 41 thus appear very dark, which means that the wires 21 and 22 can be recognized particularly reliably and quickly in subsequent processing of the line scan image information or analysis image information.

The illuminating means 27 are arranged comparatively densely opposite the chip 17 so that the diffuse light allows optimal illumination of the wires 21 and 22 from all sides. The illuminating means 27 are also arranged in an inclined manner in relation to the surface 14 of the substrate 13. Depending on which of the light-emitting diodes of the illuminating means 27 are activated, polychromatic or monochromatic homogenous light can be generated. Owing to the arrangement of the diffuser 36, it becomes possible that a formation of shadows, which might make image processing of the analysis image information more difficult, is avoided. The line scan camera 28, the illuminating means 27 and the slit projection means 25 are adjustable; i.e., they can be changed and fixed at will in terms of their distance and inclination in relation to the product 12. In this way, it becomes possible to flexibly analyze a plurality of products having different geometries and dimensions.

Figure 4:
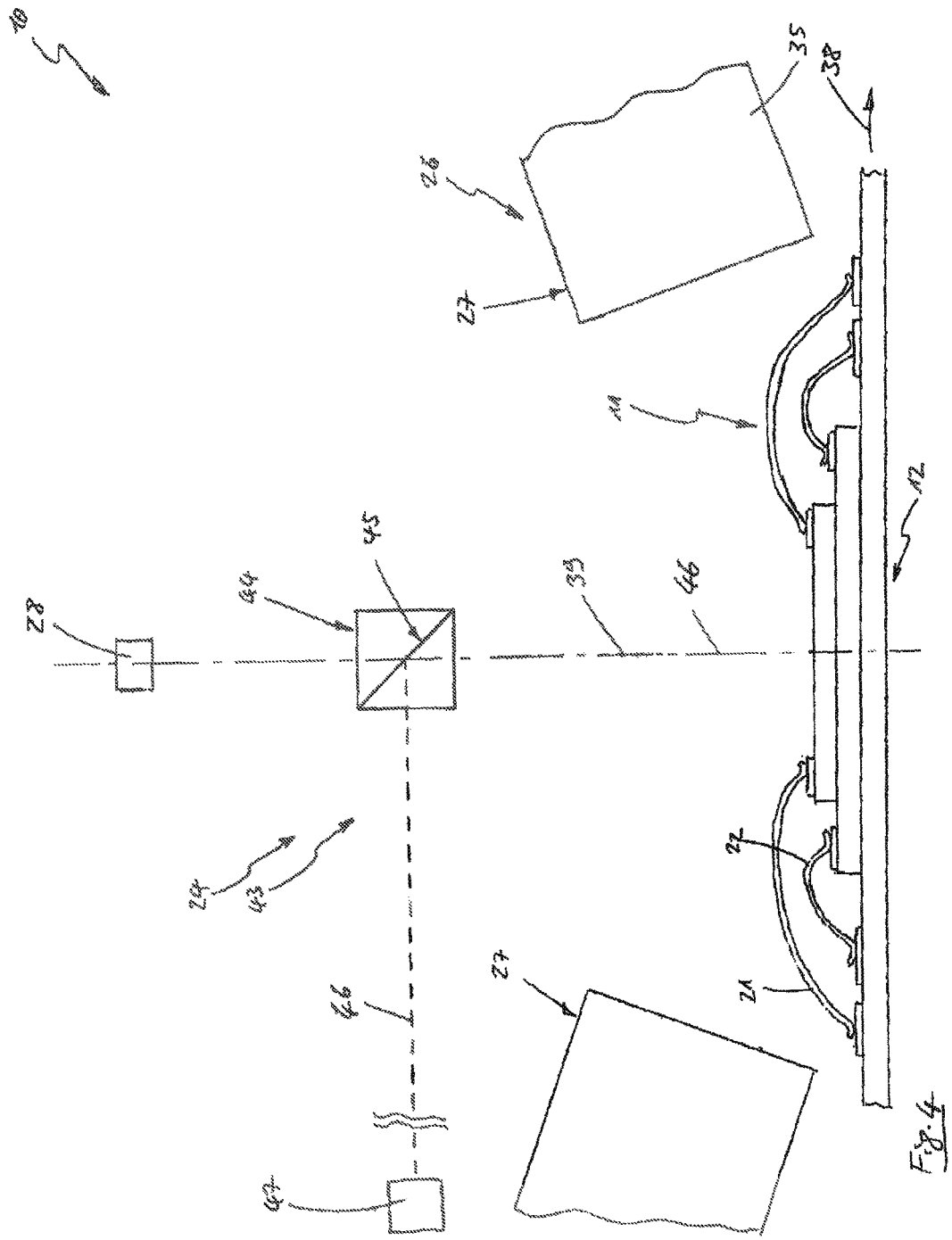
FIG. 4 shows a schematic diagram of the inspection system in a lateral view.
Figure 5:
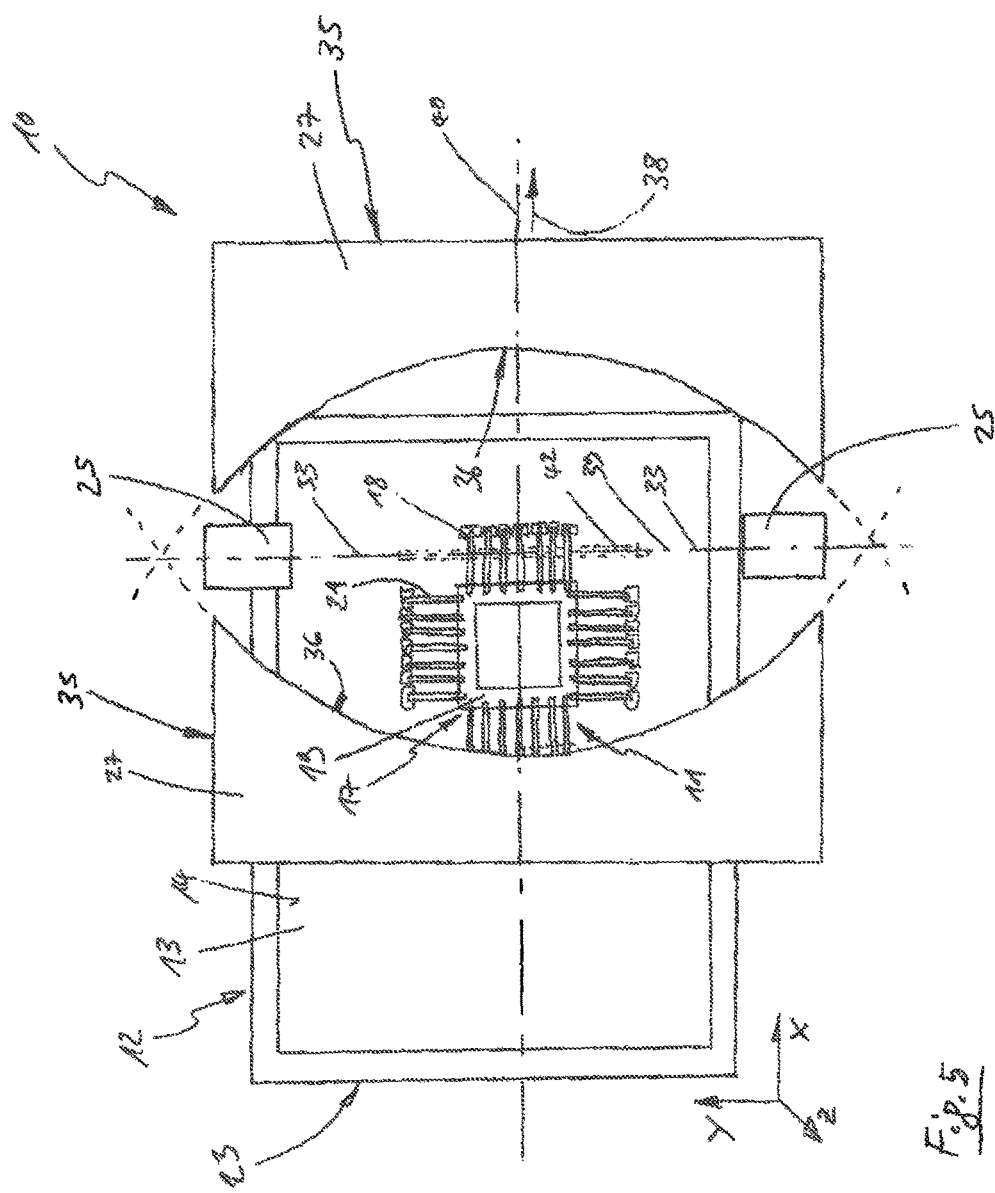
FIG. 5 shows a schematic diagram of the inspection system in a top view.
Figure 6:
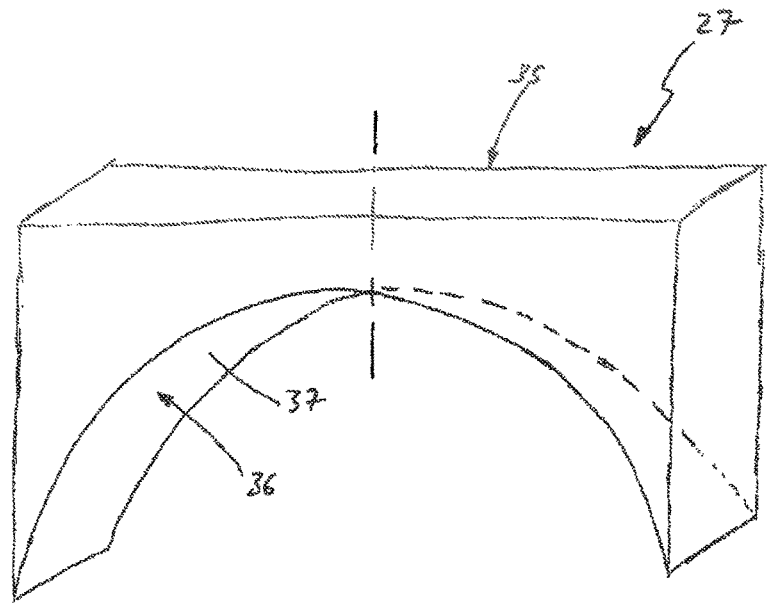
FIG. 6 shows a perspective illustration of an illuminating means.
Figure 7:
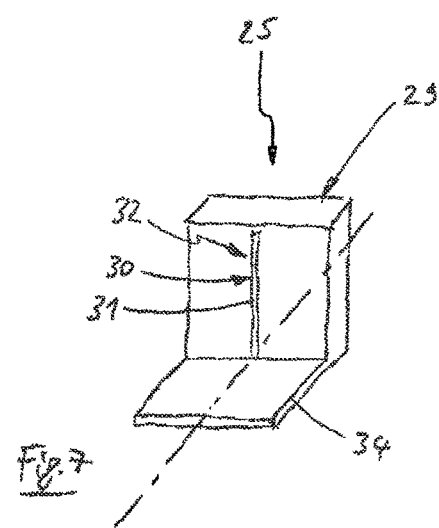
FIG. 7 shows a perspective illustration of a slit projection means.

FIG. 4 shows a slit projection means 43 of the first projection device 24, which can be part of the first projection device 24 on its own as well as together with the slit projection means 25 and vice-versa. The slit projection means 43 is arranged parallel in relation to the line scan camera 28 and has a rod-shaped prism assembly 44, which forms a partially transparent mirror 45. The prism arrangement 44 is arranged within the detection plane 39 between the line scan camera 28 and the product 12. A light slit 46, which extends parallel to the product 12 in this case and completely fills a width of the detection plane 39, is projected onto the prism assembly 44 from the housing 47 having a light source (not illustrated) of the first projection device 24. The light slit 46 is deflected by 90° and coupled into the detection plane 39 by the partially transparent mirror 45. A total reflection of the light slit 46 on the product 12 can be detected by the line scan camera 28 through the partially transparent mirror 45. The wires 21 and 22 thus appear very dark, which means that they can be recognized particularly reliably and quickly in subsequent processing of the line scan image information or analysis image information.

When the wire connections 11 are scanned, the detection plane 39 can be limited to an analysis area 42, which encloses at least the wire connections 11 and does not substantially extend beyond that. In this way, an even quicker defect analysis can be performed. In a first pass or scan of the product 12, the product 2 is moved in steps of 3 μm from a first position to a second position and further to the end position, line scan image information being registered in each position by means of the line scan camera 28. The analysis area 42 is illuminated directly by means of the first projection device 24, and subsequently or previously, the analysis area 42 is illuminated by means of the second projection device 26, line scan image information being recorded in each case. The processing device forms analysis image information of the product 12 from the plurality of line scan image information of the respective positions by superimposition. By a scan in the direction of an X-axis of the product 12, the wires 21 and 22 running parallel to the line scan camera 28 are analyzed at first, the product 12 being turned by 90° in a subsequent scan so that the wires 21 and 22 then running parallel to the line scan camera 28 are analyzed. Accordingly, the product 12 is first scanned along its X-axis and subsequently along its Y-axis. In this way, it becomes possible to also recognize comparatively thin wires 21 and 22 with 18 μm diameter, for example, by means of the line scan camera 28 at a lower resolution by superimposing the line scan image information and distances of the respective positions to record line scan image information. In a longitudinal direction of the wires 21 and 22, however, an improved resolution of the line scan camera 28 by superimposition of line scan image information is not necessary. Wires 21 and 22 running perpendicularly to the detection plane 39 can thus be scanned without superimposition of the line scan image information, which accelerates a defect analysis even further.

REFERENCE SIGNS 10 inspection system
11 wire connection
12 product
13 substrate
14 surface
15 semiconductor component
16 semiconductor component
17 chip
18 terminal face
19 terminal face
20 surface
21 wire
22 wire
23 housing
24 first projection device
25 slit projection means
26 second projection device
27 illuminating means
28 line scan camera
29 support
30 light guide assembly
31 slit
32 aperture diaphragm
33 light slit
34 screening shade
35 housing
36 diffuser
37 plastic film
38 arrow
39 detection plane
40 path of movement
41 area
42 analysis area
43 slit projection means
44 prism assembly
45 mirror
46 light slit
47 housing

The invention claimed is:
1. An inspection system for defect analysis of a wire connection between a substrate and a semiconductor component of a product, the inspection system comprising:

a first projection device;
a line scan camera; and
a processing device;
wherein the first projection device includes at least one slit projection, wherein the slit projection projects a light slit onto a wire of the wire connection between the substrate and the semiconductor component of the product, wherein light of the light slit is reflected from the wire in a detection plane of the line scan camera which extends perpendicularly from a surface of the substrate and is detected by the line scan camera, wherein the processing device derives analysis image information of the product from a plurality of line scan image information of the line scan camera,
wherein the slit projection is arranged in relation to the line scan camera in such a manner that the light slit can be projected onto the product so as to extend within the detection plane, the inspection system comprising a second projection device, the second projection device having at least one illuminating component, the illuminating component being capable of projecting diffuse light onto the product, light of the diffuse light reflected by the product in the detection plane being detectable by the line scan camera; and
wherein the slit projection is arranged laterally perpendicularly in relation to the line scan camera, the light slit being projectable onto the wire, and the semiconductor component being unlit by the light slit.

2. The inspection system according to claim 1, wherein the line scan camera is arranged perpendicularly to a direction of movement of the product, the detection plane extending parallel or perpendicularly to the wire.

3. The inspection system according to claim 1,
wherein the slit projection has at least one screening shade for blocking the light slit from the semiconductor component and/or from the substrate, the light slit being projectable onto the wire at an acute angle α in relation to a surface of the product.

4. The inspection system according to claim 1 wherein the slit projection has an assembly of optical elements, an aperture diaphragm and/or a light guide assembly, the light slit being a collimated light slit.

5. The inspection system according to claim 1 wherein the illuminating component has an arc-shaped diffuser, the arc-shaped diffuser being arranged parallel in relation to the line scan camera.

6. The inspection system according to claim 1 wherein the illuminating component has a plane diffuser, the plane diffuser being arranged parallel in relation to the product.

7. The inspection system according to claim 1 wherein the illuminating component has a light guide assembly or light-emitting diodes in an arc-shaped and/or plane arrangement.

8. The inspection system according to claim 1 wherein the illuminating component and/or the slit projection can emit light in the wavelength ranges red, green and blue (RGB), infrared (IR) and/or ultraviolet (UV).

9. The inspection system according to claim 1 wherein primary colors can be detected by the line scan camera, information regarding a surface of the product being derivable from a color value of the line scan image information by the processing device.

10. The inspection system according to claim 1 wherein the first projection device has a second slit projection, and that the second projection device has a second illuminating component, the first and second slit projection and the first and second illuminating components being arranged coaxially in relation to the line scan camera.

11. The inspection system according to claim 1 wherein the inspection system has another line scan camera, the other line scan camera being arranged parallel to the line scan camera.

12. A method for defect analysis of a wire connection between a substrate and a semiconductor component of a product using an inspection system, the method comprising:
projecting, using a first projection device having at least one slit projection, a light slit onto a wire of the wire connection, wherein light of the light slit is reflected from the wire in a detection plane of a line scan camera that extends perpendicularly to a surface of the substrate, wherein the semiconductor component is unlit by the light slit;
detecting, by the line scan camera, the light of the light slit reflected from the wire;
deriving, by a processing device, analysis image information of the product from a plurality of line scan image information of the line scan camera; and
projecting, by a second projection device having at least one illuminating component, diffuse light onto the product, wherein light of the diffuse light reflected by the product in the detection plane is detected by the line scan camera.

13. The method according to claim 12, further comprising superimposing an offset on the plurality of line scan image information of the line scan camera in a direction of movement of the product by the processing device, the offset being smaller than a physical image resolution of the line scan camera.

14. The method according to claim 12, further comprising:
moving the product at least once laterally or vertically in relation to the line scan camera;
optically scanning the product; and
obtaining analysis image information associated with the projection devices.

15. The method according to claim 12, further comprising:
optically scanning the product in at least two planes of a Z-axis of the product.

16. The method according to claim 12, further comprising:
projecting the light of the first and second projection devices onto the product in a time sequence, and synchronizing the line scan camera with the projection devices.

17. The method according to claim 12, further comprising:
obtaining height information and/or geometrical information of the wire by the processing device from a distribution of the light beam reflected by a surface of the wire.

18. The method according to claim 12, further comprising:
analyzing the light of the diffuse light reflected by the product by the processing device in terms of hue, brightness and/or saturation.

19. The method according to claim 12, further comprising:
superimposing analysis image information associated with the projection devices; and
evaluating, by the processing device the superimposed analysis image information.

* * * * *